United States Patent [19]
Rankin et al.

[11] Patent Number: 5,106,481
[45] Date of Patent: Apr. 21, 1992

[54] LINEAR AIR/FUEL SENSOR

[75] Inventors: James S. Rankin, Farmington Hills; Alex D. Colvin, Oak Park, both of Mich.

[73] Assignee: Ford Motor Company, Dearborn, Mich.

[21] Appl. No.: 657,222

[22] Filed: Feb. 19, 1991

[51] Int. Cl.$^5$ .......................................... G01N 26/27
[52] U.S. Cl. .................................................. 204/426
[58] Field of Search ....................................... 204/426

[56] References Cited

U.S. PATENT DOCUMENTS

| | | | |
|---|---|---|---|
| 4,231,733 | 11/1980 | Hickam et al. | 204/426 |
| 4,306,957 | 12/1981 | Ishitani et al. | 204/426 |
| 4,472,262 | 9/1984 | Kondo et al. | 204/426 |
| 4,576,705 | 3/1986 | Kondo et al. | 204/426 |
| 4,609,452 | 9/1986 | Shimomura | 204/426 |
| 4,609,453 | 9/1986 | Shimomura et al. | 204/426 |
| 4,622,126 | 11/1986 | Shimomura et al. | 204/426 |
| 4,626,338 | 12/1986 | Kondo et al. | 204/426 |
| 4,742,808 | 5/1988 | Blümel et al. | 204/426 |
| 4,804,454 | 2/1989 | Asakura et al. | 204/426 |
| 4,818,362 | 4/1989 | Asakura et al. | 204/426 |
| 4,839,018 | 6/1989 | Yamada et al. | 204/426 |

Primary Examiner—John Niebling
Assistant Examiner—Bruce F. Bell

[57] ABSTRACT

A method and apparatus for linearly determining the air/fuel ratio of an internal combustion engine by measuring the oxygen concentration of the exhaust gases provides a linear air/fuel output signal from a single sensor. The sensor is time shared between a current driving or oxygen pumping mode in which a current is applied to the sensor to pump oxygen through the sensor toward one or the other surface, and a voltage sensing mode in which the voltage across the sensor is monitored. A time share circuit switches between the two modes of operation. During the current mode, the oxygen concentration is changed at the sensor surface by the passage of oxygen ion current through the sensor. During the voltage mode, the sensor voltage is measured. Feedback provides necessary current during the current mode to hold the bias voltage substantially constant. The resulting current is a linear measure of the air/fuel ratio of the internal combustion engine as engine operation departs from stoichiometry. The sensor current can be positive or negative and hence will indicate both rich and lean mixtures.

7 Claims, 4 Drawing Sheets

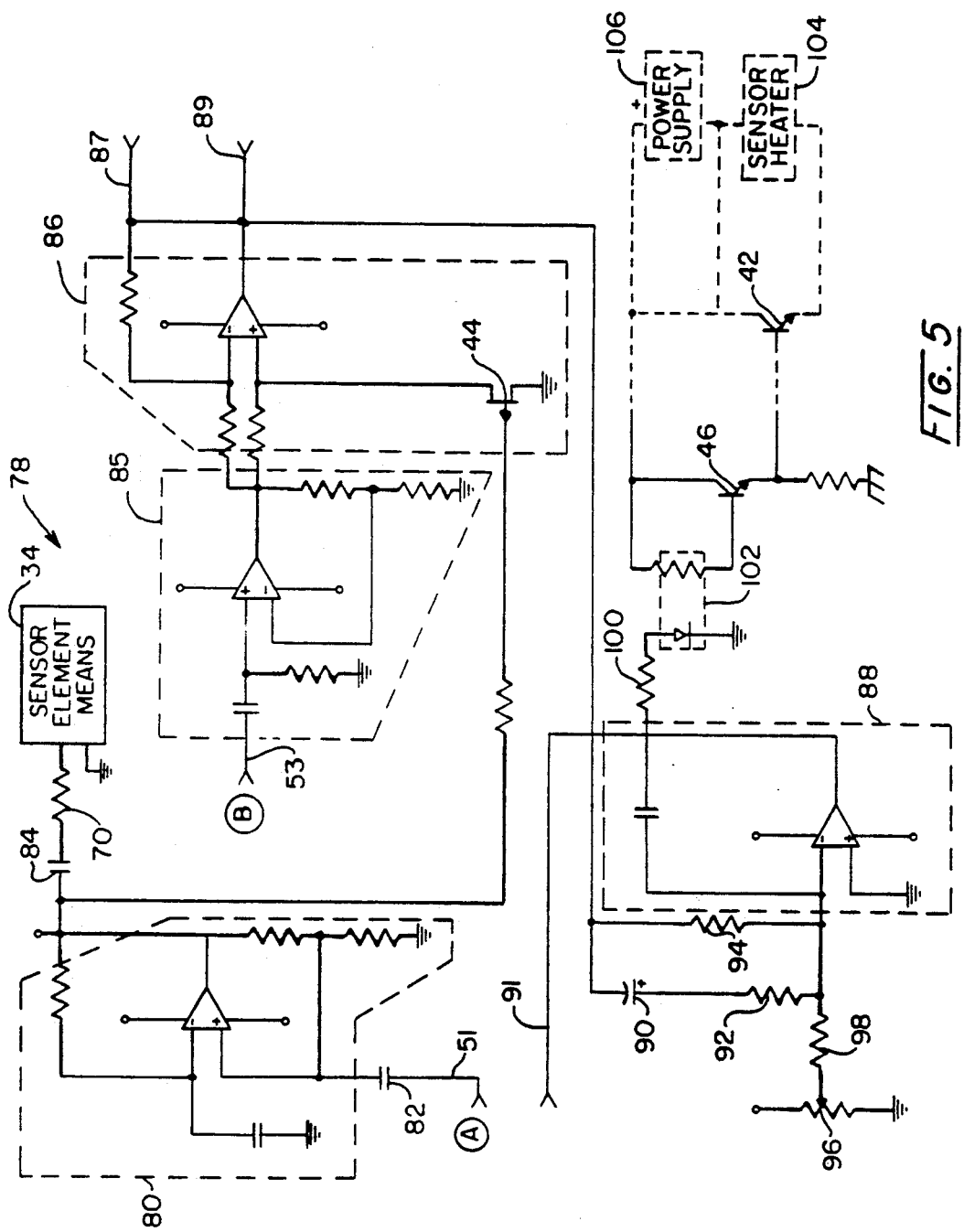

LINEAR AIR/FUEL SENSOR

BACKGROUND OF THE INVENTION

This invention relates generally to a method and apparatus for generating a linear air/fuel signal and, more particularly, to an air/fuel sensor system for an internal combustion engine and a method of operating the system in time shared voltage sensing/current driving modes.

Presently, exhaust gas sensors switch to indicate when the air/fuel mixture is rich or lean. One such sensor is the Heated Exhaust Gas Oxygen Sensor (HEGO) which has a logarithmic voltage output versus air/fuel mixture and is essentially used as a switch to indicate if the mixture is rich or lean. The HEGO has one cell and only measures the voltage across the sensor, without pumping oxygen ion current through the sensor. While the HEGO sensors normally provide a very accurate indication of rich or lean variations from stoichiometric engine operation, they cannot accurately indicate the extent of rich or lean operation of an engine as it departs from stoichiometry.

The Universal Exhaust Gas Oxygen Sensor (UEGO) does provide the desired linear signal. The sensor, however, is more expensive to produce since it has two cells and is constructed of two chambers. One cell operates as a pumping cell, wherein current applied to the cell is controlled to pump oxygen between the chambers. The resulting current can be positive or negative and will indicate both rich and lean mixtures. The second cell operates as a sensing cell to generate the sensor signal. However, the UEGO tends to have a shortened life at high exhaust manifold temperatures compared with the simpler construction of the HEGO.

One reference which discloses operation of an air/fuel sensor in a time shared manner is U.S. Pat. No. 4,716,760. This patent discloses a tubularly shaped structure comprising a solid electrolyte coupled with a diffusion resistor for measuring the air/fuel ratio of an internal combustion engine. A predetermined current is supplied to the solid electrolyte for a predetermined period of time to pump oxygen into the tubular structure the diffusion resistor. A predetermined current of the opposite polarity is then supplied to the solid electrolyte for a sufficient period of time to pump the oxygen out of the tubular structure. The time required to deplete the oxygen in the tubular structure at the boundary between the diffusion resistor and the solid electrolyte is signaled by the voltage generated across the solid electrolyte due to the difference in oxygen component pressures between the sides of the solid electrolyte. The biasing and depleting operations are performed in a repetitive manner referred to as a time sharing manner. However, the time sharing is between pumping oxygen in one direction to bias the diffusion resistor and then in the opposite direction to deplete the oxygen from the diffusion resistor.

Hence, it would be desirable to provide an air/fuel sensor system which is capable of providing an indication of the extent of rich or lean operation of an internal combustion engine as it departs from stoichiometry. It would further be desirable to provide a sensor having a linear output like the UEGO, but with the simplified construction of the HEGO.

SUMMARY OF THE INVENTION

The present invention overcomes the aforementioned problem with HEGO sensors of determining the extent of rich or lean operation of an engine as it departs from stoichiometry, and the complexity problem of the UEGO sensors, by providing a method and apparatus for linearly measuring the air/fuel ratio of an internal combustion engine. The present invention provides the linear air/fuel output signal from a single sensor which is time shared between a current driving or oxygen pumping mode in which a current is applied to the sensor to pump oxygen through the sensor toward one or the other surface, and a voltage sensing mode in which the voltage across the sensor is monitored. A time share circuit switches between the two modes of operation. During the current mode, the oxygen concentration is changed at the sensor surfaces by the passage of oxygen ion current through the sensor. During the voltage mode, the sensor voltage is measured. Feedback provides necessary current during the current mode to hold the bias voltage substantially constant. The resulting current is a linear measure of the air/fuel ratio as engine operation departs from stoichiometry. The sensor current can be positive or negative and hence will indicate both rich and lean mixtures.

The sensor system includes a sensor element made up of an oxygen-ion-conductive solid electrolyte, such as zirconium oxide $ZrO_2$, which is formed as a disk, dome, plate or the like with electrodes on opposite sides of the electrolyte. The sensor element is inserted into an exhaust of an internal combustion engine such that one surface is exposed to exhaust gases and the opposite surface is exposed to atmosphere. Such sensor elements are well known and can be utilized in air/fuel ratio measurement systems since the voltage levels developed across the sensors are dependent upon the oxygen partial pressures on the opposite sides of the sensors. In accordance with the present invention, the sensor element is time shared so that the sensor element is capable of accurately indicating not only rich or lean variations from stoichiometric engine operation, but also the extent of the rich or lean operation of the engine as it departs from stoichiometry.

In a preferred embodiment of the present invention, a sensor system for linearly determining the air/fuel ratio of an internal combustion engine by measuring the oxygen concentration in the exhaust gas comprises sensor element means having one side exposed to exhaust gases of an internal combustion engine and an opposite side exposed to atmosphere. The sensor element is used to measure oxygen partial pressures on the opposite sides thereof and generates a voltage thereacross representative of the ratio of the partial pressures of oxygen on the opposite sides thereof and being responsive to current applied thereto to convey oxygen from one side to the other dependent upon the polarity of the current applied. Voltage sensor means are provided for sensing the voltage across the sensor element means and current driver means are provided for applying current to the sensor element means. Feedback means coupled between the voltage sensor means and the current sensor means control the current driver means to apply current of proper polarity and magnitude to maintain the voltage across the sensor element means at a predetermined level. The voltage sensor means and the current driver means are alternately connected to the sensor element means to operate the sensor system in a time sharing mode between current driving and voltage sensing. Current level monitoring means monitor the current applied by the current driver means to generate an air/fuel signal which is represented by the current.

The present invention also provides a method for operating a sensor system for linearly determining the air/fuel ratio of an internal combustion engine by measuring the oxygen concentration in the exhaust gas wherein an oxygen-ion-conductive solid electrolyte sensor is supported to have one side exposed to the exhaust gases and an opposite side exposed to atmosphere. The method comprises the steps of: measuring the voltage across the sensor; applying current of sufficient magnitude and polarity to the sensor such that the voltage measured across the sensor is substantially maintained at a predetermined level; repetitively switching between the steps of measuring the voltage across the sensor and applying current to the sensor to operate the sensor in a time shared manner; and monitoring the current applied to the sensor to generate a signal representative of the oxygen content in exhaust gases for determining the air/fuel ratio of an internal combustion engine.

In accordance with preferred embodiments, it is a feature of the present invention to provide a method and apparatus for linearly measuring the air/fuel ratio of an internal combustion engine; to provide an air/fuel sensor system for an internal combustion engine; to provide a method of operating the air/fuel sensor system in time shared voltage sensing/current driving modes; and, to provide a sensor which accurately indicates the extent of rich or lean operation of an engine as it departs from stoichiometry.

Other features and advantages of the invention will become apparent from the following description, the accompanying drawings, and the appended claims.

BRIEF DESCRIPTION OF THE DRAWINGS

FIG. 5 is a schematic block diagram of a temperature control circuit which may be used in conjunction with the circuit of FIG. 4 to control or monitor the temperature of the sensor heater.

DETAILED DESCRIPTION OF THE INVENTION

Figure 1:
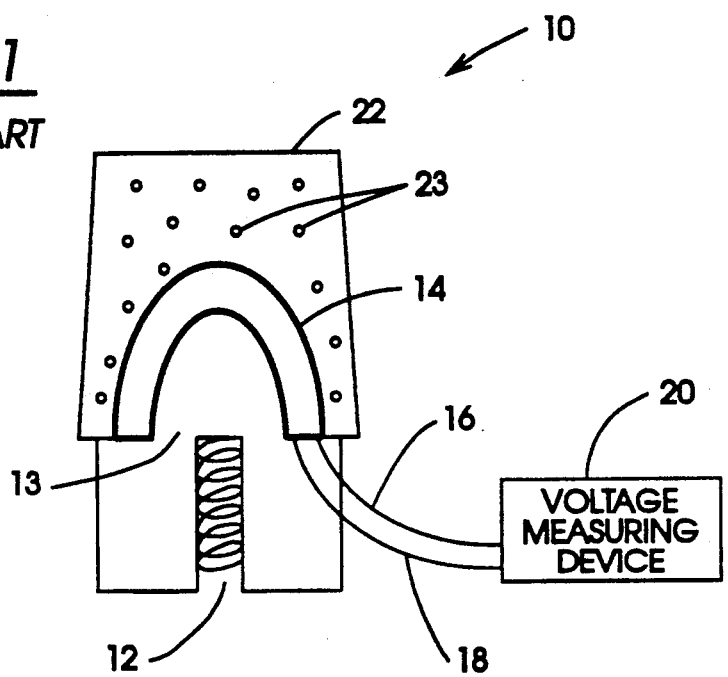
FIG. 1 is a schematic representation of an existing Heated Exhaust Gas Oxygen Sensor (HEGO)

Referring to the drawings and, more particularly, to FIG. 1, a Heated Exhaust Gas Oxygen Sensor (HEGO), generally referred to as reference numeral 10, is illustrated. The HEGO 10 derives its name from the heater unit 12. An area of reference air 13 is created between the heater 12 and a cell 14. In the HEGO 10, an oxygen sensor 14, typically a zirconium oxide ($ZrO_2$) electrochemical cell, is used for control of the air/fuel ratio of an internal combustion engine. The HEGO 10 has a logarithmic output and is essentially used as a switch to indicate if the mixture is rich or lean. The HEGO 10 only measures voltage, which voltage is measured at one end of the cell 14 via lines 16 and 18 which connect to a voltage measuring device 20. The HEGO 10 may be surrounded by a cover, such as a metal cover 22, and an area of trapped volume will then be created above the cell 14 and within the cover 22, while the exhaust emissions will be outside of the metal cover 22. This trapped volume can be diffused through one or more apertures 23 to form a diffusion resistor and allow oxygen to be pumped back and forth across the cell 14, thereby defining the infiltration rate of the exhaust gases. However, in some instances, the logarithmic output does not provide the desired amount of information, such as that provided by a linear signal.

Figure 2A:
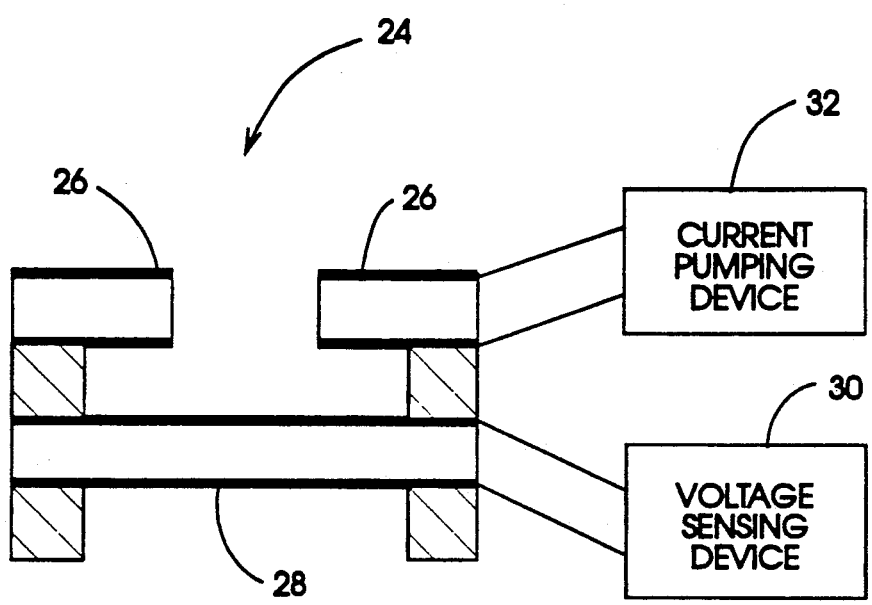
FIGS. 2A and 2B are schematic representations of an existing Universal Exhaust Gas Oxygen Sensor (UEGO)
Figure 2B:
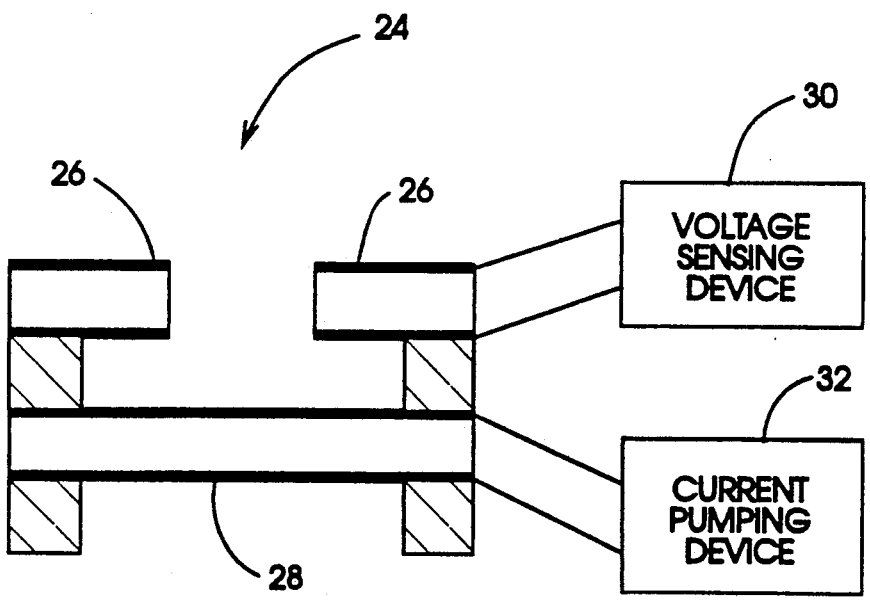

The Universal Gas Oxygen Sensor (UEGO), shown in FIGS. 2A and 2B, provides a linear signal. However, the UEGO, generally designated as reference numeral 24, is more expensive to produce since it is constructed of two cells, 26 and 28, one of which operates as a pumping cell and the other of which operates as a sensing cell. The cell 28 can be used as a conventional Nernst cell around stoichiometry or as a pump for rich or lean operation. As a result, the UEGO can indicate not only whether the engine operation is rich or lean, but also the extent of rich or lean operation of the engine as it departs from stoichiometry.

FIGS. 2A and 2B illustrate the two methods of operating the UEGO using a voltage sensing device 30 and a current pumping device 32. In FIG. 2A, the voltage is sensed at both sides of the cell 28 by the voltage sensing device 30, in order to determine the rich or lean operation of the engine. In FIG. 2B, the current pumping device 32 is applied at cell 28 to pump oxygen from one side of the cell 28 to the other side. Although the linear output of the UEGO is preferred in many applications, the UEGO is more complex and expensive than the HEGO. Additionally, the UEGO tends to have a shortened life at high exhaust manifold temperatures compared with the simpler HEGO.

Figure 3:
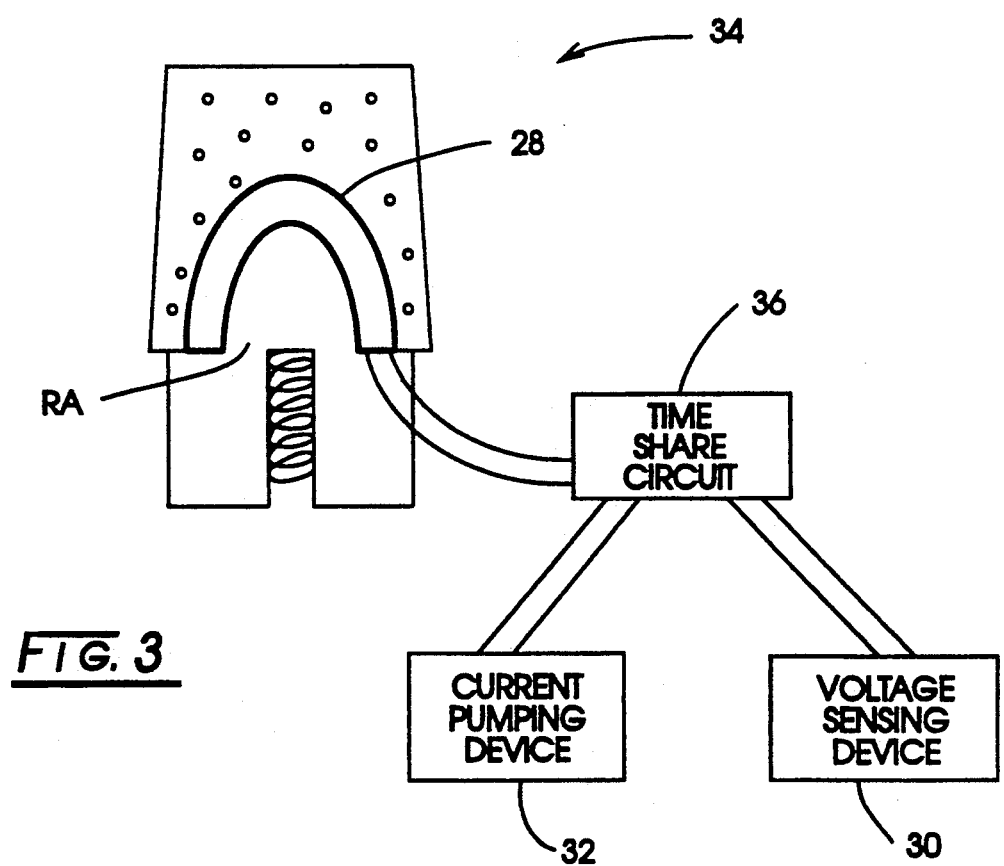
FIG. 3 is a schematic representation of the present invention which utilizes a HEGO as shown in FIG. 1 to produce the linear output of the UEGO shown in FIGS. 2A and 2B.

Referring now to FIG. 3, the present invention provides an apparatus for using the HEGO of FIG. 1 to provide the linear output of the UEGO of FIGS. 2A and 2B. The time share sensor 34 uses a circuit 36 which time shares the current pumping operation 32 and the voltage sensing operation 30. During the current mode 32, the oxygen concentration is changed at the sensor cavity since the current operates the cell to pump oxygen into or out of the cavity from the reference air RA. During the voltage mode 30, the sensor voltage, or bias voltage, of the cell is measured. Feedback provides the necessary current during the current mode 32 to hold the bias voltage substantially constant. The resulting pumping current is a linear measure of the exhaust gas oxygen concentration for determining the air/fuel ratio of an internal combustion engine.

Figure 4:
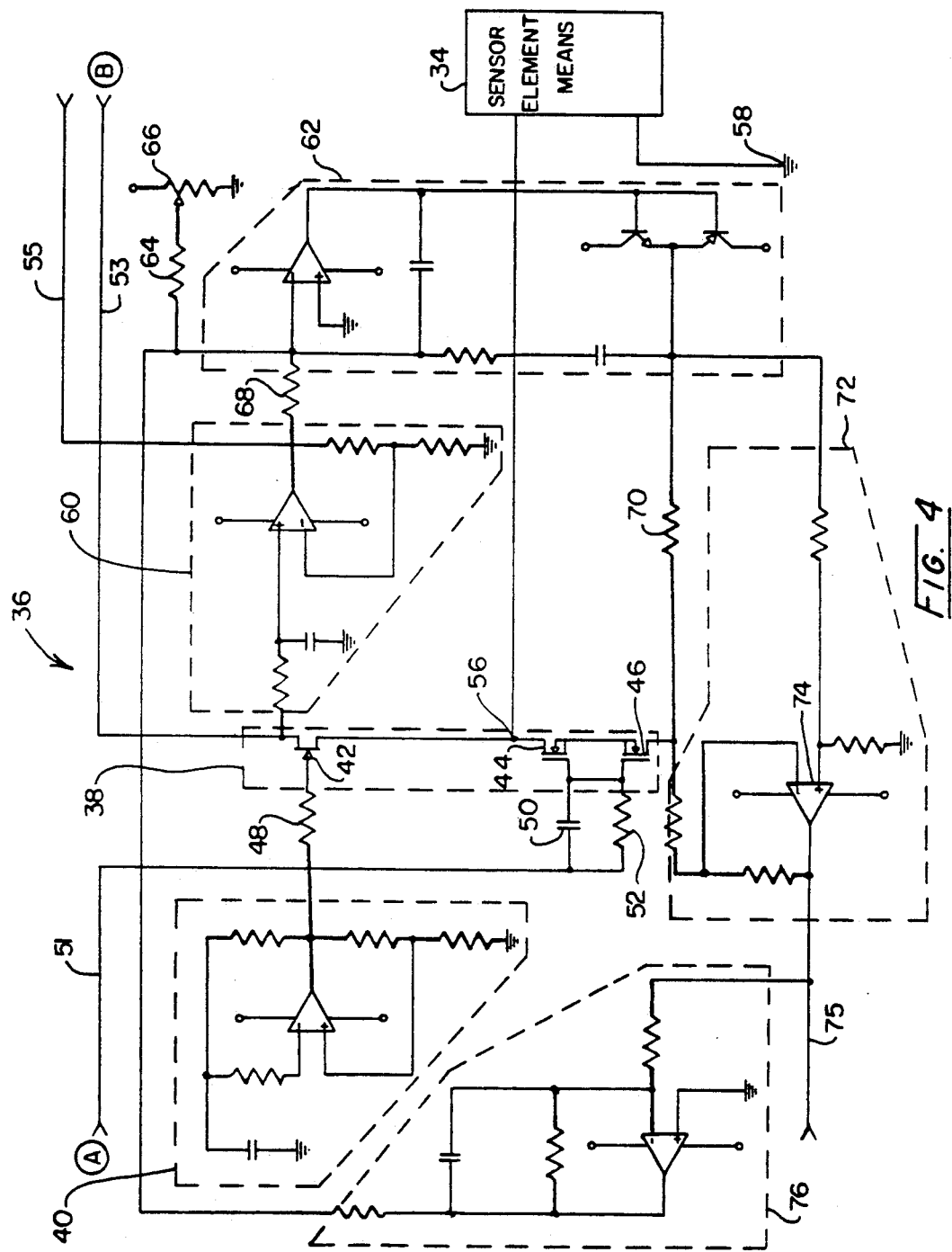
FIG. 4 is a schematic block diagram of the time share circuit utilized by the present invention of FIG. 3.

FIG. 4 is a schematic diagram of the air/fuel time share circuit 36 of the present invention which utilizes switching means 38 to control the time sharing operation. As with the UEGO, the sensor circuit 36 current can be positive or negative and will indicate the extent of both rich or lean operation of the engine. In FIG. 4, a time share square wave oscillator 40 produces a square wave capable of turning FET switches 42, 44, and 46, of switching means 38, on and off through resistor 48, capacitor 50, and resistor 52, respectively. The output of the oscillator 40 is also provided on line 51 to FIG. 5, as described below. Associated with switching means 38 is a voltage and temperature signal which is generated on line 53 and provided by the circuitry of FIG. 5, as described below. The sensor element 34 of FIG. 3, preferably made up of an oxygen-ion-conductive solid electrolyte, such as Zirconia, is attached between connector 56 and ground 58, such that one surface is exposed to exhaust gases and the opposite surface is exposed to atmosphere.

The air/fuel time share circuit 36 further includes a bias amplifier circuit 60 operating as voltage sensor means for reading the sensor element 34 voltage through the FET switch 42, and outputting the sensor 34 voltage via line 55. FET switch 42 samples the voltage from sensor 34 for half the time, that is, when current is not flowing in the sensor 34. A current driver means or sensor current drive circuit 62 receives a reference signal from resistors 64 and 66, and the voltage signal from resistor 68. From these signals, the current drive circuit 62 produces an output voltage which drives current through a current sampling resistor 70 and through FET switches 44 and 46, for the other half of the time, to the sensor 34. Hence, the FET switches 42, 44, and 46 operate as switching means 38 for alternately connecting the voltage sensor means 60 and the current driver means 62 to the sensor element means 34 to operate the sensor system in a time sharing mode between current driving and voltage sensing.

A difference amplifier circuit 72, operating as a current level monitoring means, reads the current signal by taking the difference of the voltage across the current sampling resistor 70. The output voltage of operating amplifier 74, then, is the desired linear air/fuel signal which signal is output on line 75. Also, the current feedback circuit or feedback means 76 is included in a preferred embodiment of the air/fuel time share circuit 36 for use if a different bias voltage is desired for rich or lean engine operation as well as providing necessary current during the current mode to hold the bias voltage substantially constant.

FIG. 5 illustrates a temperature control circuit 78 which may be used with the air/fuel time share circuit 36 of FIG. 4. In the temperature control circuit 78, an oscillator 80 produces a square wave synchronized through capacitor 82 from the oscillator 40 of FIG. 4, via line 51. A square wave ac coupled current signal is introduced into the sensor element means 34 of FIG. 4 through capacitor 84 and resistor 70. This current signal produces a voltage in the sensor 34 depending on the resistance of the sensor 34 which is a very sensitive measure of the temperature of the sensor.

In the temperature control circuit 78, the sensor 34 voltage signal on line 53 of FIG. 4 is amplified at amplifier 85 and synchronously detected with reference to a square wave generator voltage. A synchronous detector 86 produces a voltage indicative of the resistance and, thus, the temperature, of the sensor 34. A temperature signal is output on line 87, and a temperature indicator signal is output on line 89.

Finally, an integrator or heater driver amplifier 88 receives the resistance signal from capacitor 90 and resistors 92 and 94, and compares it to the temperature reference signal from resistors 96 and 98. The drive signal output on line 91 is coupled through resistor 100 to an optical isolator 102 to drive FET switch 46 which, in turn, drives the FET switch 42. The FET switch 42 then provides power to the sensor heater 104 from an external power supply or battery 106.

Having described the invention in detail and by way of reference to preferred embodiments thereof, it will be apparent that other modifications and variations are possible without departing from the scope of the invention defined in the appended claims.

What is claimed is:

1. A sensor system for linearly determining the air/fuel ratio of an internal combustion engine by measuring the oxygen concentration in the exhaust gases, the system comprising:

sensor element means comprising a single sensor cell having one side exposed to exhaust gases of an internal combustion engine and an opposite side exposed to atmosphere for measuring oxygen partial pressures on said opposite sides of said sensor element means, said sensor element means generating a voltage thereacross representative of the ratio of the partial pressures of oxygen on said opposite sides thereof and being responsive to current applied thereto to convey oxygen from one side to the other dependent upon the polarity of the current applied;

voltage sensor means for sensing the voltage across said sensor element means;

current driver means for applying positive and negative polarity current to said sensor element means;

feedback means coupled between said voltage sensor means and said current sensor means for controlling said current driver means to apply current of proper polarity and magnitude to maintain the voltage across said sensor element means at a predetermined level;

switching means coupled to said sensor element means for alternately connecting said voltage sensor means and said current driver means to said sensor element means to operate said sensor system in a time sharing oscillatory mode alternating between current driving and voltage sensing; and current level monitoring means coupled to said current drive means and said feedback means for monitoring the current applied by said current driver means to generate an air/fuel signal which is represented by said current.

2. A sensor system for linearly determining the air/fuel ratio of an internal combustion engine as claimed in claim 1 wherein the signal sensor cell of said sensor element means comprises an oxygen-ion-conductive solid electrolyte such as zirconium oxide.

3. A circuit having a time sharing oscillatory operation for use with a single exhaust gas oxygen sensor cell having one side exposed to exhaust gases of an internal combustion engine and an opposite side exposed to atmosphere, the circuit providing a linear output of exhaust gas oxygen concentration of an internal combustion engine, the circuit comprising: a current drive portion for pumping oxygen into or out of the exhaust gases;

a voltage sensing circuit for sensing a bias voltage of the exhaust gas oxygen sensor cell; and feedback means for providing current from said current drive portion to hold said bias voltage substantially constant, whereby a resulting pumping current represents a linear measure of exhaust gas oxygen concentration.

4. A circuit as claimed in claim 3 further comprising oscillatory switching means for controlling the time sharing operation.

5. A circuit as claimed in claim 3 further comprising a temperature control circuit for determining the temperature of the exhaust gas oxygen sensor cell, said temperature control circuit comprising an oscillator for generating a square wave current signal, a capacitor for coupling said square wave current signal to the exhaust gas oxygen sensor cell, and detector means responsive to the resultant square wave voltage for generating a voltage signal which is representative of the temperature of the exhaust gas oxygen sensor cell.

6. A method for operating a sensor system for linearly determining the air/fuel ratio of an internal combustion engine by measuring the oxygen concentration of exhaust gases of the engine, wherein a single oxygen-ion-conductive solid electrolyte sensor is supported to have one side exposed to the exhaust gases and an opposite side exposed to atmosphere comprising the steps of:

measuring the voltage across said sensor;

applying current of sufficient magnitude and polarity to said sensor such that the voltage measured across said sensor is substantially maintained at a predetermined level;

repetitively switching between the steps of measuring the voltage across said sensor and applying current to said sensor to operate said sensor in a time shared manner; and monitored the current applied to said sensor to generate a signal representative of the oxygen concentration of the exhaust gases for determining the air/fuel ratio of the internal combustion engine.

7. A circuit as claimed in claim 5 wherein said temperature control circuit further provides for controlling the temperature of said exhaust gas oxygen sensor cell and further comprises a sensor cell heater, and heater driver amplifier means for comparing said voltage signal to a temperature reference signal to generate a temperature control drive signal, said sensor cell heating being responsive to said temperature control drive signal to maintain the temperature of said sensor cell at an operating temperature.

* * * * *